（12） United States Patent
Chiu

(10) Patent No.: US 9,364,182 B2
(45) Date of Patent: Jun. 14, 2016

(54) PULSE MEASUREMENT DEVICES FOR BIO-SIGNALS

(71) Applicant: MAISENSE INC., Zhubei (TW)

(72) Inventor: Benjamin Chiu, Zhubei (TW)

(73) Assignee: Maisense Inc., Zhubei, Hsinchu County (TW)

( * ) Notice: Subject to any disclaimer, the term of this patent is extended or adjusted under 35 U.S.C. 154(b) by 560 days.

(21) Appl. No.: 13/846,328

(22) Filed: Mar. 18, 2013

(65) Prior Publication Data

US 2014/0276113 A1    Sep. 18, 2014

(51) Int. Cl.
*A61B 5/00* (2006.01)
*A61B 5/024* (2006.01)
*A61B 5/021* (2006.01)

(52) U.S. Cl.
CPC ............... *A61B 5/6842* (2013.01); *A61B 5/021* (2013.01); *A61B 5/02416* (2013.01); *A61B 5/681* (2013.01); *A61B 2560/0276* (2013.01)

(58) Field of Classification Search
CPC .............. A61B 2560/0276; A61B 5/02416; A61B 5/681; A61B 5/6842; A61B 5/021; A61B 5/022; A61B 5/024; A61B 5/06
See application file for complete search history.

(56) References Cited

U.S. PATENT DOCUMENTS

| 4,224,948 | A | 9/1980 | Cramer et al. |
| 6,631,282 | B2* | 10/2003 | Rule ................... A61B 5/061 600/344 |
| 2009/0022272 | A1 | 1/2009 | Joseph et al. |
| 2009/0306524 | A1* | 12/2009 | Muhlsteff ........... A61B 5/021 600/485 |

FOREIGN PATENT DOCUMENTS

| JP | 2005270546 A | 10/2006 |
| JP | 4392279 B2 | 12/2009 |
| WO | WO03/082101 A1 | 10/2003 |
| WO | WO2009/141769 A1 | 11/2009 |

OTHER PUBLICATIONS

European Search Report dated May 21, 2014, as issued in Europe Patent Application No. 13173723.1.

* cited by examiner

*Primary Examiner* — Christian Jang
(74) *Attorney, Agent, or Firm* — Muncy, Geissler, Olds & Lowe, P.C.

(57) ABSTRACT

A measurement device is provided for measuring a vessel pulse signal of a specific position attached by a mark. The measurement device includes a sensor, a plurality of conductive dots, a determination unit, and a measurement unit. The conductive dots are located around the sensor. The determination unit determines whether the plurality of conductive dots are connected to each other through the mark to generate a determination signal to indicate whether the sensor has been disposed in the specific position.

20 Claims, 11 Drawing Sheets

PULSE MEASUREMENT DEVICES FOR BIO-SIGNALS

BACKGROUND OF THE INVENTION

1. Field of the Invention

The invention relates to a measurement device, and more particularly to a measurement device which can sense the same position of an object to measure a vessel pulse signal every time.

2. Description of the Related Art

With aging societies, more and more burden is being placed on hospital resources. Moreover, cardiovascular diseases are increasing, as people age and stress increases for modern day living. For example, high blood pressure is a normal symptom of cardiovascular diseases. Thus, bio-signal self-measurement measurement devices have become an important target for development in the healthcare industry. Through bio-signal self-measurement manners, patients can monitor their own physiology status anytime, to relieve strain on hospital resources and provide needed medical attention to patients.

Signals generated by bio-signal self-measurement devices highly depend on the positions of the human body touched by sensors of the bio-signal self-measurement devices. If a patient performs continuous or long-term bio-signal measurement by a bio-signal self-measurement device, it is important to make sure that a sensor of the bio-signal self-measurement device always touches the same position of the patient for accurate determination of physiology status. Some prior arts provide a measurement device with a sensor array to sense vessel pulse waveforms of an object. Due to the sensor array, a desired position of the object can be easily touched every time. However, the sensor array increases the cost and volume of the measurement device.

BRIEF SUMMARY OF THE INVENTION

Thus, it is desirable to provide a measurement device which can measure a vessel pulse signal from the same desired position of an object every time. Moreover, the measurement device should have a sensor and be light and portable.

An exemplary embodiment of a measurement device is provided. The measurement device is used to measure a vessel pulse signal of a specific position of an object. A mark is attached on the specific position. The measurement device comprises a sensor, a plurality of conductive dots, a determination unit, and a measurement unit. The conductive dots are located around the sensor. The determination unit determines whether the plurality of conductive dots are connected to each other through the mark to generate a determination signal to indicate whether the sensor has been disposed in the specific position.

An exemplary embodiment of a measurement system is provided. The measurement system measures a vessel pulse signal of a specific position of an object. The measurement system comprises a mark, a sensor, a plurality of conductive dots, a determination unit, and a measurement unit. The mark is attached on the specific position. The conductive dots are located around the sensor. The determination unit determines whether the plurality of conductive dots are connected to each other through the mark to generate a determination signal to indicate whether the sensor has been disposed in the specific position.

A detailed description is given hereafter embodiments with reference to the accompanying drawings.

BRIEF DESCRIPTION OF THE DRAWINGS

The invention can be more fully understood by reading the subsequent detailed description and examples with references made to the accompanying drawings, wherein.

DETAILED DESCRIPTION OF THE INVENTION

The following description is of the best-contemplated made of carrying out the invention. This description is made for the purpose of illustrating the general principles of the invention and should not be taken in a limiting sense. The scope of the invention is best determined by reference to the appended claims.

Figure 1A:
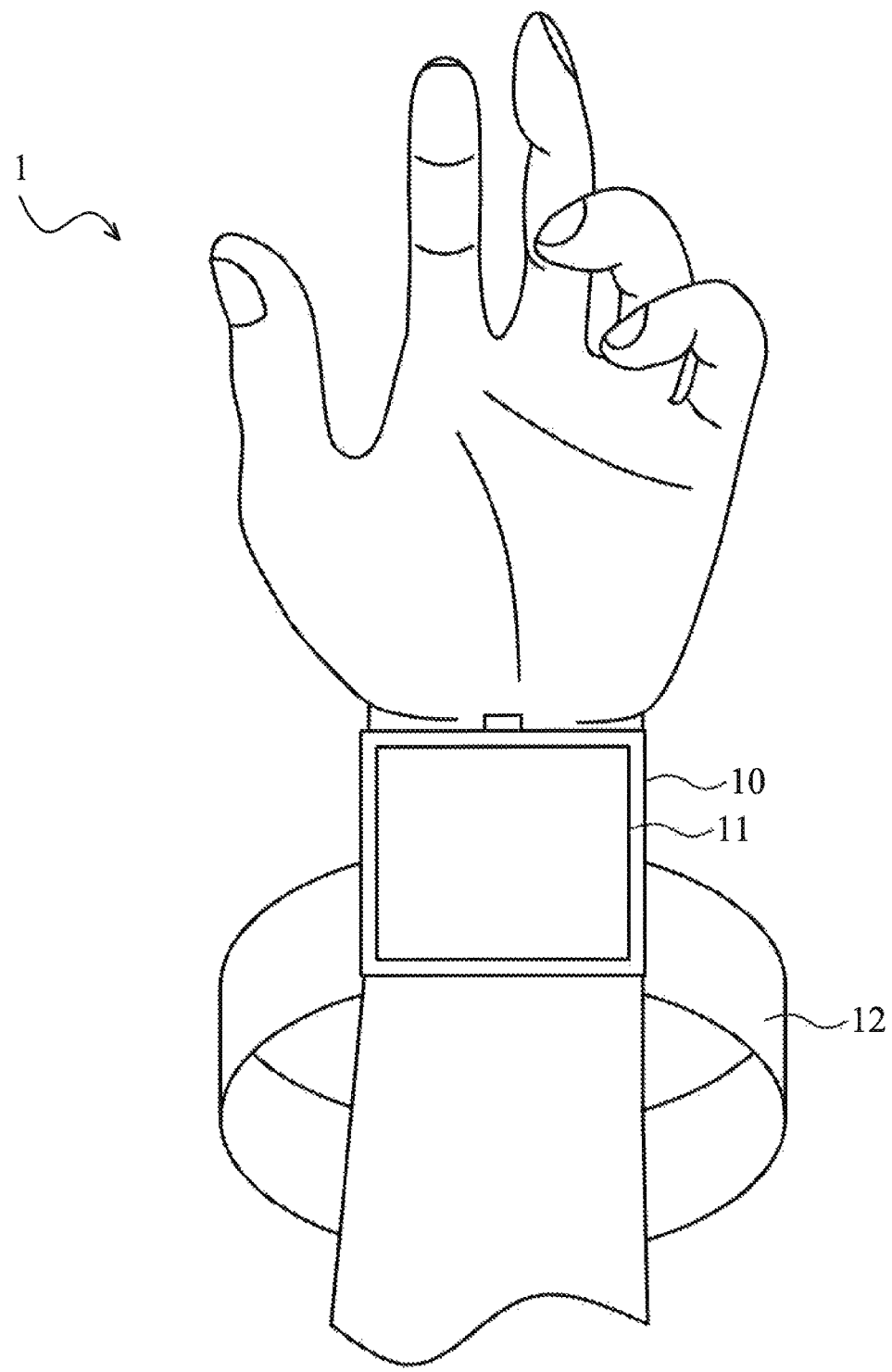
FIG. 1A shows the appearance of an exemplary embodiment of a measurement device.
Figure 1B:
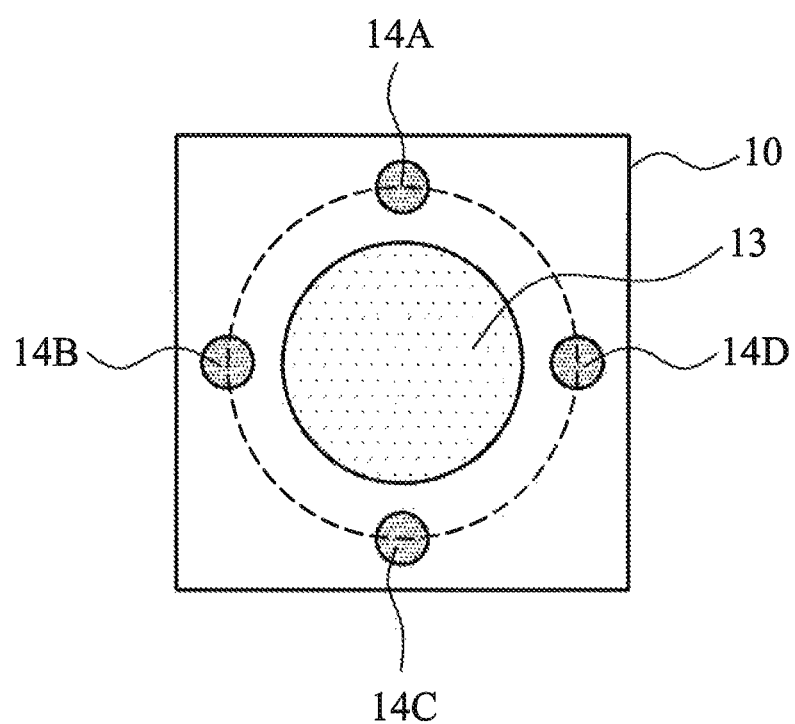
FIG. 1B shows a sensor and conductive dots of the measurement device in FIG. 1A.

FIG. 1A shows the appearance of an exemplary embodiment of a measurement device, and FIG. 1B shows a side view of the measurement device in FIG. 1A. Referring to FIG. 1A, when viewing the appearance of a measurement device 1, the measurement device 1 comprises a case 10, a displayer 11, and a bracelet 12. The case 10 is disposed on the bracelet 12. The case 10 has an inner side and an outer side. When the measurement device 1 has been placed on a specific position of an object (such as the wrist) of a user to measure vessel pulse signals, the measurement device 1 is tied onto the specific position of the object through the bracelet 12, and, at this time, the inner side of the case 10 faces the specific position of the object. Referring to FIG. 1B, the measurement device 1 further comprises a sensor 13 and a plurality of conductive dots. In the embodiment of FIGS. 1A and 1B, four conductive dots 14A-14D are given as an example for illustration. The sensor 13 is used to sense a vessel pulse waveform of a specific position of the object, for example a position on the skin over the radial artery at the wrist. The conductive dots 14A-14D are located around the sensor 13. As shown in FIG. 1B, the conductive dots 14A-14D are dispersed to four positions which are at the same distance from the sensor 13. Moreover, by taking the sensor 13 as a reference point, two adjacent conductive dots (such as 14A and 14B) are symmetrical to the other two adjacent conductive dots (such as 14C and 14D). In the embodiment, the sensor 13 can be implemented by a pressure sensor or a photo plethysmograph (PPG).

Figure 2:
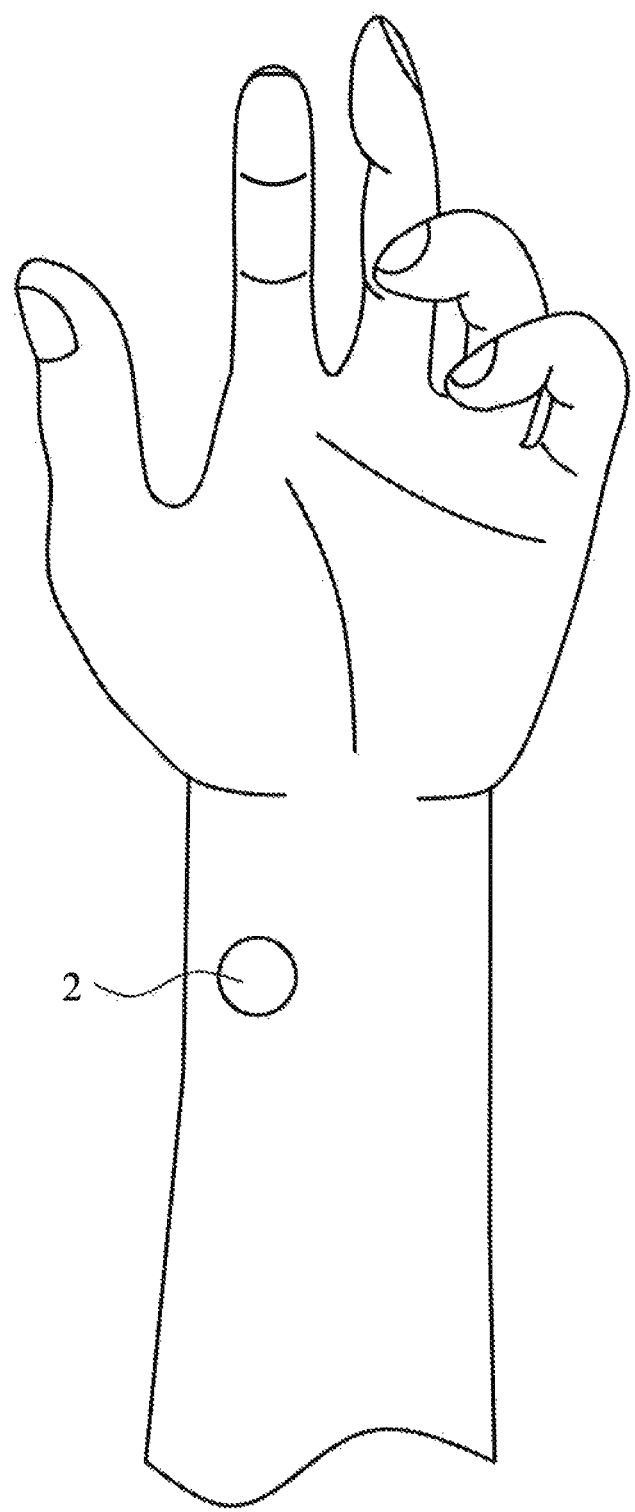
FIG. 2 is a schematic view showing a specific position where a mark is attached.
Figure 3:
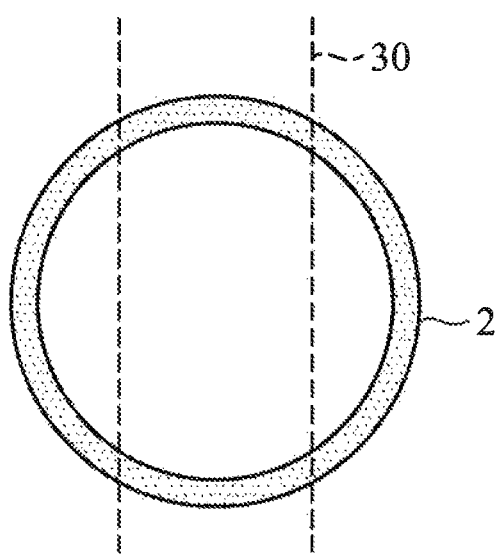
FIG. 3 is a schematic view showing an exemplary embodiment of a shape of a mark.

Before the measurement device 1 begins to measure a vessel pulse signal of the specific position, a mark is required to be attached on the specific position. For example, as shown in FIG. 2, a mark 2 is attached on a position on the skin over the radial artery at the wrist. The specific position is predetermined. In an embodiment, the specific position is predetermined by a professional physician. The mark 2 is made of a conductive material and further is bio-compatible with the skin. In an embodiment, the mark 2 is implemented by a conductive ink, and the conductive Ink is printed on the specific position by a stamp. In another embodiment, the mark 2 is implemented by a metal film, and one side of the metal film has a tape for touching the skin of the specific position when the mark 2 is attached on the specific position. Regarding the shape of the mark 2, the mark 2 has a circular shape. In an embodiment, the mark 2 has a hollow circular shape, as shown in FIG. 3. The mark 2 with the hollow circular shape is attached on the specific position on the skin over the radial artery 30.

In the embodiment, the configuration of the conductive dots 14A-14D matches the shape of the mark 2. For example, referring back to FIG. 1B, the conductive dots 14A-14D define a circle which represented by a dotted line, wherein the conductive dots 14A-14D are disposed on the circumference of the circle. The circle defined by the conductive dots 14A-14D match the hollow circular shape of the mark 2. In the embodiment, due to the hollow circular shape of the mark 2, when the sensor 13 is correctly disposed in the specific position, the sensor 13 can directly touch the skin of the wrist. In an embodiment, the diameter of the circle defined by the conductive dots 14A-14D is equal to the diameter of the hollow circular shape of the mark 2.

In an embodiment, the mark 2 and the measurement device 1 form a measurement system for measuring a vessel pulse signal of a specific position of an object. Hereafter, the detailed structure and operation of the measurement system of the embodiment will be described by taking a position on the skin over the radial artery at the wrist as an example of the specific position (hereafter referred to as "specific position").

Figure 4:
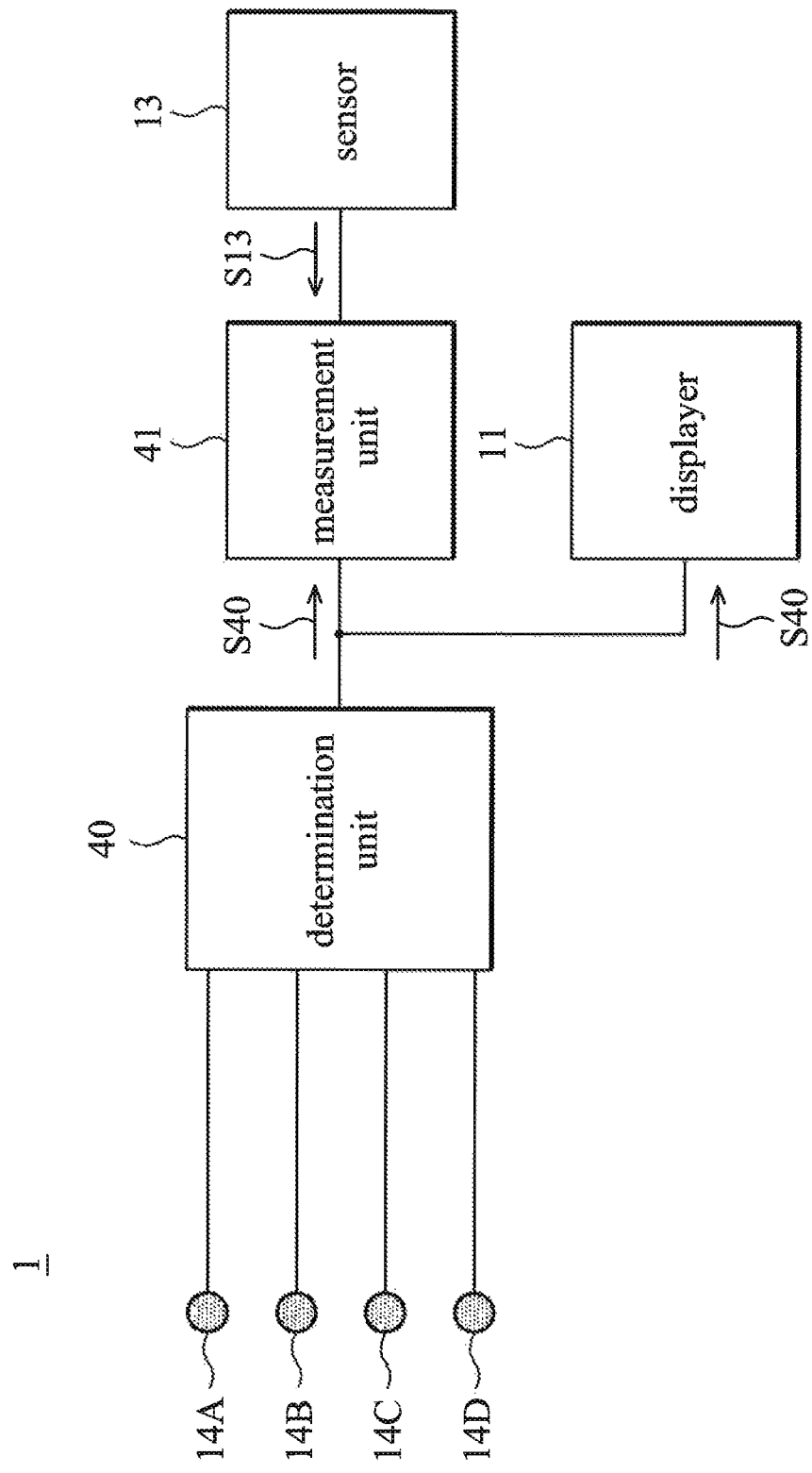
FIG. 4 is a schematic block diagram of the measurement device in FIG. 1A

FIG. 4 shows a block diagram of the measurement device 1. The case 10, the displayer 11, the bracelet 12, the sensor 13, and the conductive dots 14A-14D shown in FIGS. 1A and 1B are the devices or elements which are observed from the appearance of the measurement device 1. Referring to FIG. 4, the measurement device 1 further comprises a determination unit 40 and a measurement unit 41. FIG. 4 does not show the case 10, the bracelet 12, and sensor 13, however, they are shown in FIGS. 1A and 1B.

Figure 5B:
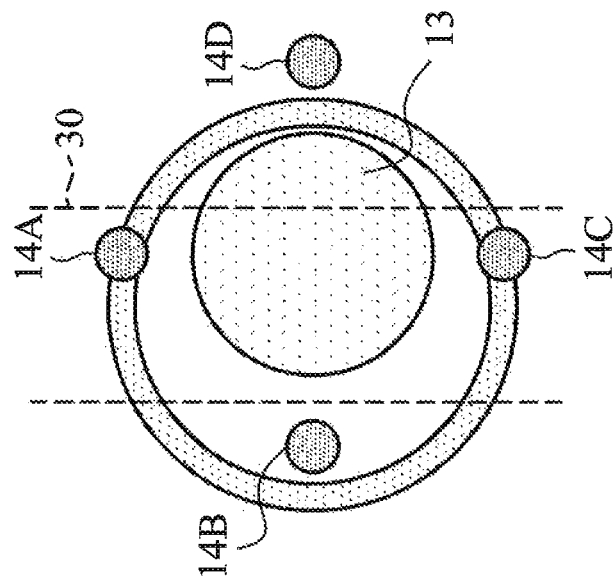
FIG. 5A-5C are schematic views showing a location relationship between a mark and four conductive dots according to an exemplary embodiment.
Figure 5A:
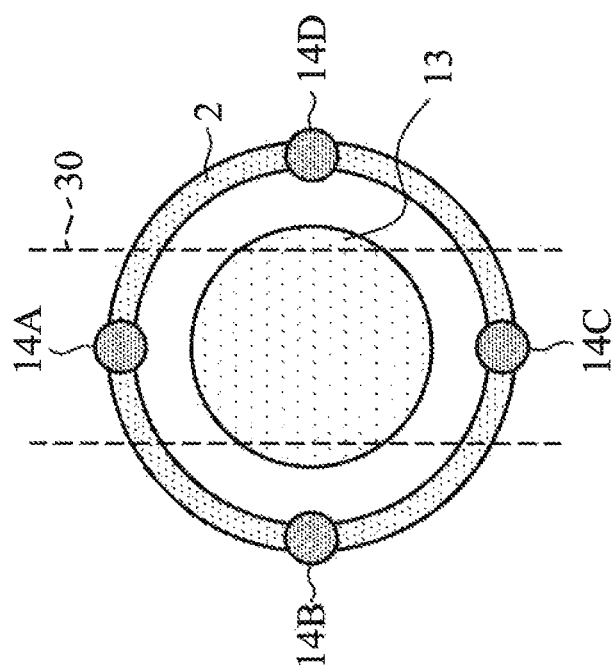
Figure 5C:
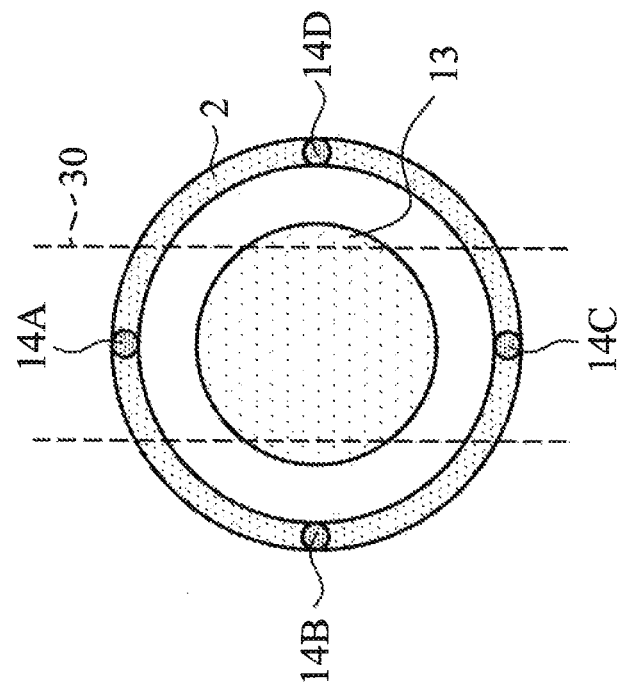
Figure 5D:
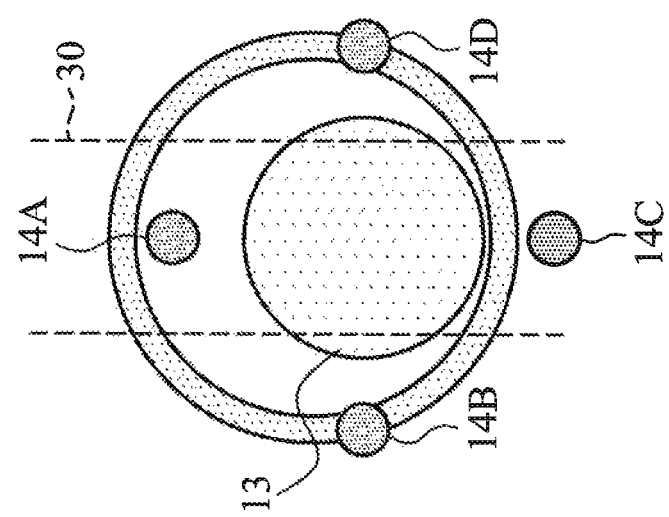
FIG. 5D shows an example of the size of the mark and conductive dots in FIGS. 5A-5C.

When the measurement device 1 is required to measure a vessel pulse signal of the specific position, the sensor 13 has to be accurately disposed in the position where the mark 2 is attached. According to the embodiment, when the sensor 13 touches at the wrist, the determination unit 40 determines whether the conductive dots 14A-14D are connected to each other to generate a determination signal S40. Since the mark 2 is conductive, the conductive dots 14A-14D will be connected to each other through the mark 2 when all of the conductive dots 14A-14D touch the mark 2, which means that the sensor 13 has been disposed in the specific position correctly. Accordingly, the determination signal S40 can indicate whether the conductive dots 14A-14D are connected to each other, that is whether the sensor 13 has been disposed in the specific position correctly. The measurement unit 41 receives the determination signal S40 and controls the sensor 13 according to the determination signal S40. When the determination unit 40 determines that the conductive dots 14A-14D are connected to each other through the mark 2, as shown in FIG. 5A, the measurement unit 41 controls the sensor 13 to sense a vessel pulse waveform of the specific position according to the determination signal S40. Then, the sensor 13 generates a vessel pulse signal S13 according to the sensing result. On the contrary, when at least one of the conductive dots 14A-14D do not touch the mark 2, the conductive dots 14A-14D will not be connected to each other through the mark 2, which means that the sensor 13 is not correctly disposed in the specific position. In other words, the position where the sensor 13 touches the wrist has shifted from the specific position, as shown in FIGS. 5B and 5C. In FIG. 5B, the position where the sensor 13 touches the wrist has shifted right from the specific position. In FIG. 5C, the position where the sensor 13 touches the wrist has shifted down from the specific position. When the determination unit 40 determines that the conductive dots 14A-14D are not connected to each other, the measurement unit 41 does not control the sensor 13 to sense a vessel pulse waveform of the specific position according to the determination signal S40. In the above embodiment, the diameter of each of the conductive dots 14A-14D is greater than the width of mark 2. In a preferred embodiment, the diameter of each of the dots 14A-14D is equal to the width of mark 2, as shown in FIG. 5D.

When the sensor 13 is controlled by the measurement unit 41 to sense the vessel pulse waveform of the specific position, the measurement unit 41 receives the vessel pulse signal S13 from the sensor 13. The measurement unit 41 then calculates some cardiovascular indexes according to the vessel pulse signal S13, such as a blood pressure value. The displayer 11 is coupled to the measurement unit 41. After the cardiovascular indexes is obtained, the displayer 11 can receive the cardiovascular indexes from the measurement unit 41 and show the received cardiovascular indexes to the user or medical staff, such as professional physicians and nurses.

In an embodiment, the displayer 11 can be further coupled to the determination unit 40 to receive the determination signal S40. As descried above, the determination signal S40 can indicate whether the conductive dots 14A-14D are connected to each other, that is whether the sensor 13 has been disposed in the specific position correctly. When the displayer 11 receives the determination signal S40, the displayer 11 can show a notification to indicate whether the conductive dots 14A-14D are connected to each other, such that the user or medical staff can know whether the sensor 13 is correctly disposed in the specific position according to the notification. In an embodiment, the notification can be achieved by a message or a flashing light.

Figure 6:
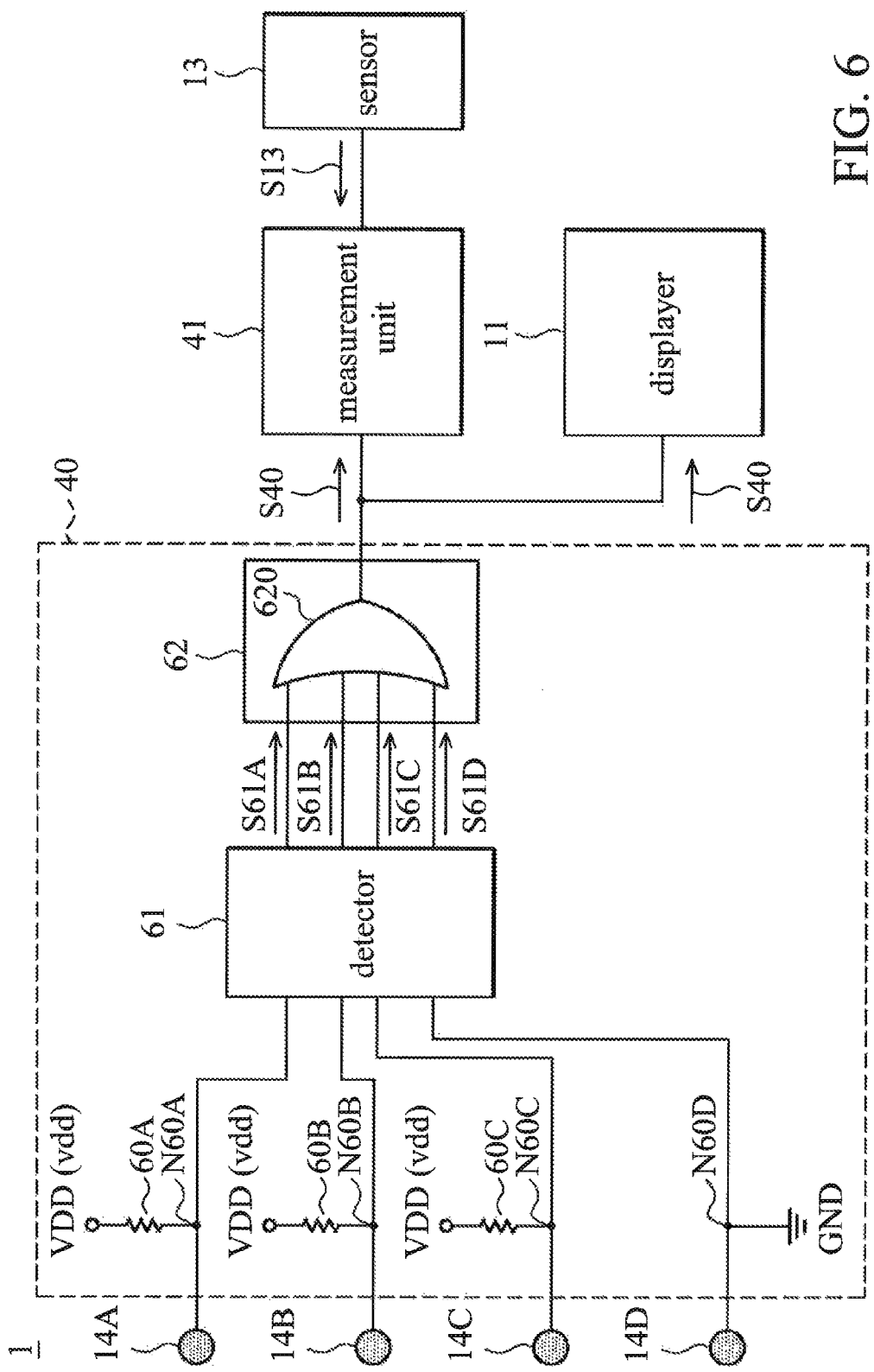
FIG. 6 shows an exemplary embodiment of a determination unit of the measurement device in FIG. 1A.

FIG. 6 shows an exemplary embodiment of the determination unit 40. As shown in FIG. 6, the determination unit 40 comprises pull-up resistors 60A-60C, a detector 61, and a determination circuit 62. One terminal of the pull-up resistor 60A is coupled to the conductive dot 14A at a node N60A, and the other terminal thereof is coupled to a voltage source VDD providing a voltage vdd. One terminal of the pull-up resistor 60B is coupled to the conductive dot 14B at a node N60B, and the other terminal thereof is coupled to the voltage source VDD. One terminal of the pull-up resistor 60C is coupled to the conductive dot 14C at a node N60C, and the other terminal thereof is coupled to the voltage source VDD. The conductive dot 14D is coupled to a reference ground GND at a node N60D, and the voltage level at the conductive dot 14D is always coupled to the voltage level of the reference ground GND. The detector 61 is coupled to the nodes N60A-N60D to detect the voltage levels at the conductive dots 14A-14D.

As shown in FIG. 5A, when all of the conductive dots 14A-14D touch the mark 2 (that is the sensor 13 has been disposed in the specific position correctly), the conductive dots 14A-14D are connected to each other through the mark 2, and all of the voltage levels at the conductive dots 14A-14C are coupled to the voltage level of the reference ground GND through the conductive dot 14D. The detector 61 detects the voltage levels at the conductive dots 14A-14D through the nodes N60A-N60D, respectively. Then, the detector 61 generates detection signals S61A-S61D according to the detection result of the voltage levels at the conductive dots 14A-14D, respectively. In the case where all of the voltage levels at the conductive dots 14A-14D are coupled to the voltage level of the reference ground GND, the values of the detection signals S61A-S61D are represented by "0", "0", "0", and "0", respectively. The determination circuit 62 receives the detection signals S61A-S61D of the values "0", "0", "0", and "0", and then generates the determination signal S40 according to the values of the detection signals S61A-S61D to indicate that the sensor 13 has been disposed in the specific position correctly. In an embodiment, the determination circuit 62 is implemented by an OR gate 620. The OR gate 620 receives the detection signals S61A-S61D of the values "0", "0", "0", and "0" to generate the determination signal S40 with the value "0".

As shown in FIG. 5B, when the position where the sensor 13 touches the wrist has shifted right from the specific position, the conductive dots 14A and 14C touch the marks 2, and, however, the conductive dots 14B and 14D do not touch the mark 2 (that is the sensor 13 is not correctly disposed in the specific position). At this time, the conductive dots 14A-14C are not connected to the conductive dot 14D, and the voltage levels at the conductive dots 14A-14C is pulled high to the level of the voltage vdd through the pull-up resistors 60A-60C, respectively. The detector 61 detects the voltage levels at the conductive dots 14A-14D through the nodes N60A-N60D, respectively to generate the detection signals S61A-S61D with the values "1", "1", "1", and "0". The OR gate 620 of determination circuit 162 receives the detection signals S61A-S61D of the values "1", "1", "1", and "0" and then generates the determination signal S40 with the value "1" according to the values of the detection signals S61A-S61D to indicate that the sensor 13 is not correctly disposed in the specific position.

As shown in FIG. 5C, when the position where the sensor 13 touches the wrist has shifted down from the specific position, the conductive dots 14B and 14D touch the marks 2, and, however, the conductive dots 14A and 14C do not touch the mark 2 (that is the sensor 13 is not correctly disposed in specific position). At this time, only the conductive dot 14B is connected to the conductive dot 14D through the mark 2, and the voltage level at the conductive dot 14B is pulled down to the voltage level of the reference ground GND through the conductive dot 14D. Since the conductive dots 14A and 14C are not connected to the conductive dot 14D through the mark 2, the voltage levels of the conductive dots 14A and 14C is pulled high to the level of the voltage vdd through the pull-up resistors 60A and 60C, respectively. The detector 61 detects the voltage levels of the conductive dots 14A-14D through the nodes N60A-N60D, respectively to generate the detection signals S61A-S61D with the values "1", "0", "1", and "0". The OR gate 620 of determination circuit 162 receives the detection signals S61A-S61D of the values "1", "0", "1", and "0" and then generates the determination signal S40 with the value "1" according to the values of the detection signals S61A-S61D to indicate that the sensor 13 is not correctly disposed in the specific position.

According to the above description, when all of the conductive dots 14A-14D touch the mark 2, the determination unit 62 generates the determination signal S40 with the value "0" to indicate that the sensor 13 has been disposed in the specific position correctly. When at least one of the conductive dots 14A-14D do not touch the mark 2, the determination unit 62 generates the determination signal S40 with the value "1" to indicate that the sensor 13 is not correctly disposed in the specific position. In response to the determination signal S40, the measurement unit 41 can control the sensor 13 to sense a vessel pulse waveform of the specific position or not.

In the determination manner of the invention, the measurement device 1 can easily measure a vessel pulse signal of the specific position every time when users desire to know their cardiovascular indexes. For long-term measurement, the measurement device 1 can measure a vessel pulse signal of the same position, which is advantageous to diagnosis of cardiovascular diseases.

In an embodiment, the conductive dots 14A-14D can be made of a magnetic material. Accordingly, the conductive dots 14A-14D can be easily attached to the conductive mark 2, such that the sensor 13 can be easily disposed in the correct position (that is the specific position).

Figure 7B:
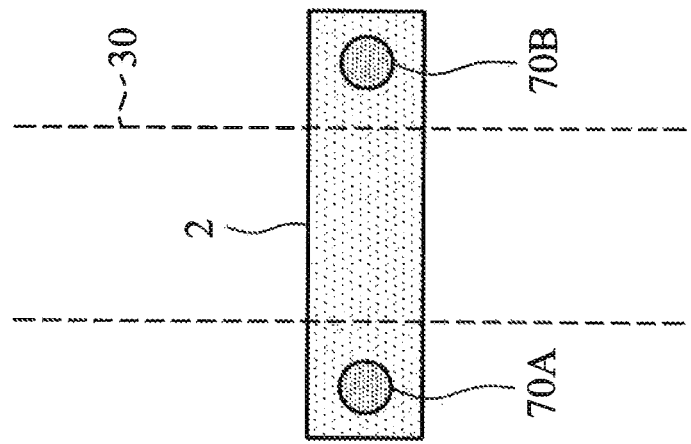
FIGS. 7B-7D are schematic views showing a location relationship between a mark and the conductive dots in FIG. 7A.
Figure 7A:
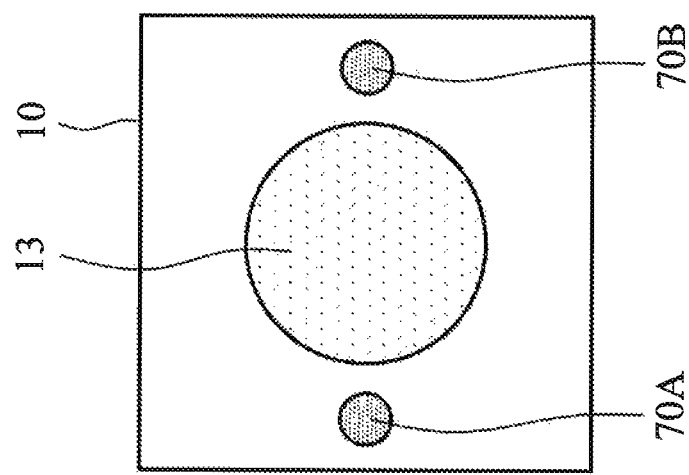
FIG. 7A shows an exemplary embodiment of conductive dots of the measurement device in FIG. 1A.
Figure 7D:
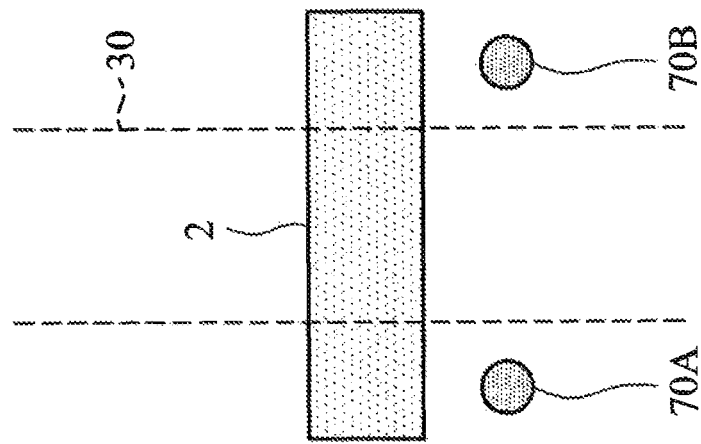
Figure 7C:
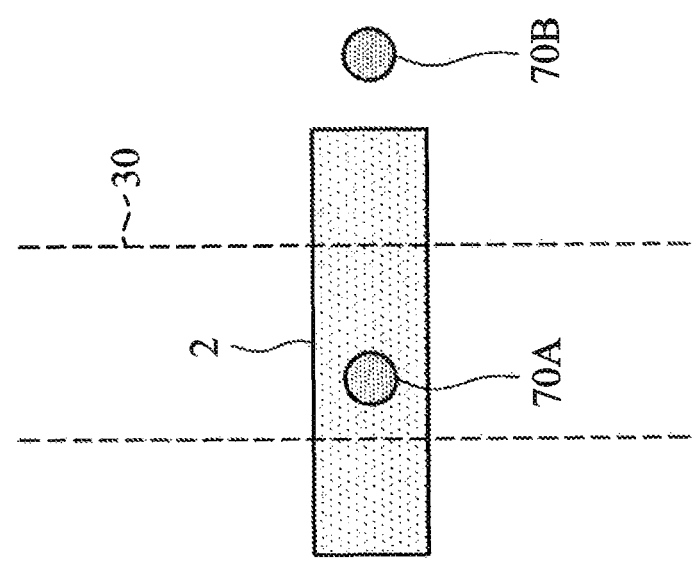
Figure 7E:
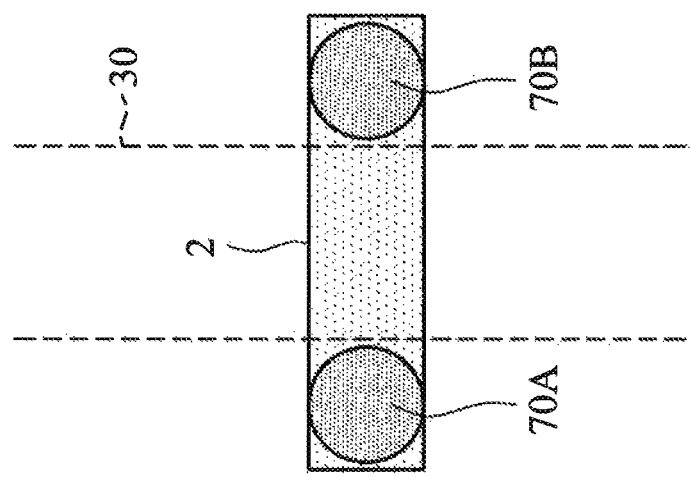
FIG. 7E shows an example of size of the mark and conductive dots in FIGS. 7B-7D.

In the above embodiment, the number of conductive dots is equal to four, and the mark 2 has a hollow circular shape. In other embodiments, the number of conductive dots can be determined according to system requirements, such as the size of the measurement device 1, and the shape of the mark 2 can be determined according to the number of conductive dots. For example, in an embodiment of FIGS. 7A-7D, there are two conductive dots 70A and 70B located around the sensor 13, and the mark 2 has a strip shape where the length is equal to the distance of the two conductive dots 70A and 70B. As shown in FIG. 7B, when both of the conductive dots 70A and 70B touch the mark 2, the conductive dots 70A and 70B are connected to each other through the mark 2, which means that the sensor 13 has been disposed in the specific position correctly. When at least one of the conductive dots 70A and 70B do not touch the mark 2, the conductive dots 70A and 70B will be connected to each other through the mark 2, which means that the sensor 13 is not correctly disposed in the specific position. In other words, the position where the sensor 13 touches the wrist has shifted from the specific position, as shown in FIGS. 7C and 7D. In FIG. 7C, the position where the sensor 13 touches the wrist has shifted right from the specific position. In FIG. 7D, the position where the sensor 13 touches the writs has shifted down from the specific position. Whether the conductive dots 70A and 70B are connected to each other through the mark 2 can be determined according to the above determination manner performed by the determination unit 40, thus, since already described, related description is omitted here. Note that, for the embodiment of FIGS. 7A-7D, the number of pull-up resistors in the determination unit 40 is decreased to one. For example, the one pull-up resistor is coupled between the conductive dot 70A and the voltage source VDD, and the conductive dot 70B is coupled to the reference ground GND. In the above embodiment, the diameter of each of the conductive dots 70A and 70B is less than the width of the strip shape of the mark 2. In a preferred embodiment, the diameter of each of the conductive dots 70A and 70B is equal to the width of the strip shape of the mark 2, and the distance between the two conductive dots 70A and 70B is equal to the length of the strip shape of the mark 2, as shown in FIG. 7E.

In an embodiment, the mark 2 in the embodiment of FIGS. 7A-7E has a curve shape. When the measurement device 1 measures the vessel pulse signal of the specific position, the mark 2 with the curve shape does not overlap with the sensor 13 when it is correctly disposed in the specific position, so that it may avoid degrading sensitivity of the sensor 13.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A measurement device for measuring a vessel pulse signal of a specific position of an object, the measurement device comprises:
    a sensor;
    a plurality of conductive dots located around the sensor and configured to be coupled to a mark, wherein the mark is configured to be attached to the specific position; and
    a determination unit determining whether the plurality of conductive dots are connected to each other through the mark to generate a determination signal to indicate whether the sensor has been disposed in the specific position.

2. The measurement device as claimed in claim 1, wherein the sensor is a pressure sensor.

3. The measurement device as claimed in claim 1, wherein the sensor is a photo plethysmograph.

4. The measurement device as claimed in claim 1, wherein the plurality of conductive dots defines a circle, and the plurality of conductive dots are disposed on the circumference of the circle.

5. The measurement device as claimed in claim 1, wherein the plurality of conductive dots are made of a magnetic material.

6. The measurement device as claimed in claim 1 further comprising:
    a measurement unit receiving the determination signal and controlling the sensor according to the determination signal,
    wherein when the determination unit determines that the plurality of conductive dots are connected to each other through the mark to generate the determination signal to indicate that the sensor has been disposed in the specific position, according to the determination signal, the measurement unit controls sensor to sense a vessel pulse waveform of the specific position to generate the vessel pulse signal.

7. The measurement device as claimed in claim 6, wherein the determination unit comprises:
    a detector, coupled to the plurality of conductive dots, detecting voltage levels at the plurality of conductive dots to generate a plurality of detection signals; and
    a determination circuit receiving the plurality of detection signals and determining whether the voltage levels at the plurality of conductive dots are equal to a voltage level of a reference ground according to the plurality of detection signals to generate the determination signal,
    wherein when the plurality of conductive dots are connected to each other through the mark, the determination circuit determines that the voltage levels at the plurality of conductive dots are equal to the voltage level of the reference ground.

8. The measurement device as claimed in claim 7, wherein the determination circuit comprises:
    an OR gate receiving the plurality of detection signals and generating the determination signal according to the plurality of detection signals.

9. The measurement device as claimed in claim 6, wherein when the sensor senses the vessel pulse waveform of the specific position to generate the vessel pulse signal, the measurement unit receives the vessel pulse signal and calculates cardiovascular indexes according to the vessel pulse signal.

10. The measurement device as claimed in claim 9, further comprising:
    a displayer, coupled to the measurement unit to receive the cardiovascular indexes, displaying the cardiovascular indexes.

11. The measurement device as claimed in claim 10,
    wherein the displayer is coupled to the determination unit to receive the determination signal, and
    wherein the displayer shows a notification according to the determination signal to indicate whether the plurality of conductive dots are connected to each other through the mark.

12. A measurement system for measuring a vessel pulse signal of a specific position of an object comprising:
    a mark configured to be attached to the specific position;
    a sensor;
    a plurality of conductive dots located around the sensor;
    a determination unit determining whether the plurality of conductive dots are connected to each other through the mark to generate a determination signal to indicate whether the sensor has been disposed in the specific position.

13. The measurement system as claimed in claim 12, wherein the mark is conductive ink.

14. The measurement system as claimed in claim 12, wherein the mark is a metal film.

15. The measurement system as claimed in claim 12, wherein the mark has a circular shape.

16. The measurement system as claimed in claim 15, wherein the plurality of conductive dots defines a circle with a diameter of the mark with the circular shape, and the plurality of conductive dots are disposed on the circumference of the circle.

17. The measurement system as claimed in claim 12, wherein the mark has a curve shape.

18. The measurement system as claimed in claim 12 further comprising:
    a measurement unit receiving the determination signal and controlling the sensor according to the determination signal,
    wherein when the determination unit determines that the plurality of conductive dots are connected to each other through the mark to generate the determination signal to indicate that the sensor has been disposed in the specific position, according to the determination signal, the measurement unit controls the sensor to sense a vessel pulse waveform of the specific position to generate the vessel pulse signal.

19. The measurement system as claimed in claim 18, wherein the determination unit comprises:
    a detector, coupled to the plurality of conductive dots, detecting voltage levels at the plurality of conductive dots to generate a plurality of detection signals; and
    a determination circuit receiving the plurality of detection signals and determining whether the voltage levels at the plurality of conductive dots are equal to a voltage level of a reference ground according to the plurality of detection signals to generate the determination signal, wherein when the plurality of conductive dots are connected to each other through the mark, the determination circuit determines that the voltage levels at the plurality of conductive dots are equal to the voltage level of the reference ground.

20. The measurement system as claimed in claim 18, wherein when the sensor senses the vessel pulse waveform of the specific position to generate the vessel pulse signal, the measurement unit receives the vessel pulse signal and calculates cardiovascular indexes according to the vessel pulse signal.

\* \* \* \* \*